(12) United States Patent
Anders et al.

(10) Patent No.: US 7,407,812 B2
(45) Date of Patent: Aug. 5, 2008

(54) METHOD AND KIT FOR THE ISOLATION OF PHOSPHORYLATED PEPTIDES

(75) Inventors: Jonas Anders, Darmstadt (DE); Achim Schwämmle, Darmstadt (DE); Sven Andrecht, Griesheim (DE); Robertus Hendriks, Heidelberg (DE); Anette Boerner, Darmstadt (DE); Cora Rueter, Berlin (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/596,251

(22) PCT Filed: Apr. 21, 2005

(86) PCT No.: PCT/EP2005/004272

§ 371 (c)(1),
(2), (4) Date: Nov. 13, 2006

(87) PCT Pub. No.: WO2005/111062

PCT Pub. Date: Nov. 24, 2005

(65) Prior Publication Data

US 2007/0227974 A1    Oct. 4, 2007

(30) Foreign Application Priority Data

May 14, 2004    (EP)    ................... 04011468

(51) Int. Cl.
*C07K 1/22*    (2006.01)
(52) U.S. Cl. ....................................... 436/174
(58) Field of Classification Search .............. 436/174
See application file for complete search history.

(56) References Cited

OTHER PUBLICATIONS

Andrecht, S. et al. Specific and efficient enrichment of phosphopeptides for phospho-proteome analysis by mass spectrometry, Jul. 24, 2006, Merck KGaA, Life Sciences & Analytics R&D.*
Battles, Sean, Sigma-Aldrich Lunches New PhosphoProfile (TM) I Phosphopeptide Enrichment Kit, Sep. 11, 2006, Thomas Net.*
ProteoExtract(TM) Phosphopeptide Capture Kit, Calbiochem, Jun. 23, 2005, pp. 1-6.*
D.E. Kalume, et al., "Tacking the phosphoproteome: tools and strategies", Current Opionion in Chemical Biology, (2003), pp. 64-69.
Vladka Gaberc-Porekar, et al., "Perspectives of immonilized-metal affinity chromatography", Journal of Biochemical and Biophysical Methods, (2002), pp. 335-360.

(Continued)

*Primary Examiner*—Walter D. Griffin
*Assistant Examiner*—Christine T Mui
(74) *Attorney, Agent, or Firm*—Millen, White, Zelano, Branigan, P.C.

(57) ABSTRACT

The invention relates to a method and a kit for the isolation of phosphorylated peptides from complex mixtures using support materials having chelate ligands based on silica and alkaline elution buffers. In preferred embodiments, the method according to the invention enables the isolation of phosphopeptides from complex sample solutions with a reproducibly high yield and at the same time with high purity and it allows efficient ionisation and detection of the isolated phosphopeptides both by MALDI-TOF and also by ESI mass spectrometry without additional requisite method steps, such as, for example, chromatographic desalination of the sample.

11 Claims, 7 Drawing Sheets

OTHER PUBLICATIONS

Jerker Porath, et al.; Immobilized Metal Ion Affinity Adsorption and Immobilized Metal Ion . . . Biochemistry, (1983), pp. 1621-1630.

E. Hochuli, et al., "New Metal Chelate Adsorbent Selective for Proteins and Peptides Containing Neighbouring Histidine Residues", Journal of Chromatography, (1987), pp. 177-184.

Azita Kaffashan et al., "Evaluation of Commercially Available IMAC Kits: Millipore ZipTip . . . ", ASMS Conference on Mass Spectrometry and Allied Topics, (2003), Montreal, Canada.

Dimitri Heintz, et al., "An efficient protocol for the identification of protein phosphorylation in a seedless plant . . . " Electrophoresis, (2004), pp. 1149-1159.

René Massart, Preparatioan of Aqueous Magnetic Liquides in Alkaline and Acidic Media, IEEE Transactions on Magnetics, vol., Mag. 17, No. 2, (1981), pp. 1247-1248.

Tadao Sugimoto et al., "Formation of Uniform Spherical Magnetite Particles by Crystallization from Ferrous Hydroxide Gels[1]", Journal of Colloid and Interface Science, (1980), pp. 227-243.

Qu et al., Magnetite Nanoparticles Prepared by Precipitation from Partially Reduced . . . , Journal of Colloid and Interface Science 215, (1999), pp. 190-192.

\* cited by examiner

METHOD AND KIT FOR THE ISOLATION OF PHOSPHORYLATED PEPTIDES

The invention relates to a method and a kit for the isolation of phosphorylated peptides from complex mixtures using support materials having chelate ligands based on silica and alkaline elution buffers. In preferred embodiments, the method according to the invention enables the isolation of phosphopeptides from complex sample solutions with a reproducibly high yield and at the same time with high purity and it allows efficient ionisation and detection of the isolated phosphopeptides both by MALDI-TOF and also by ESI mass spectrometry without additionally requisite method steps, such as, for example, chromatographic desalination of the sample.

With the sequencing of the human genome, science has gained access to the individual genetic code of each human being. This provides information on his/her descent and origin. However, this information is inadequate for investigation of the biological function of individual genes or the corresponding proteins. The complex network of a cell cannot be characterised simply by decoding the genomic DNA of a human being. The genomic analysis must be followed by an investigation of the proteins encoded by the genome, since it is only with this additional information that the dynamic functioning of the human organism can be described at a molecular level. In addition, there is frequently only a minor correlation between gene transcription and the corresponding translation product, and consequently it is only with the aid of proteome analysis that it can be determined which proteins are expressed to what extent and possibly modified post-translationally under given influences. However, quantitative analysis of the expression of a protein and the investigation of any posttranslational modifications are the basic prerequisite for understanding of the function of a particular protein.

The complexity of the cellular proteome increases exponentially if the possible posttranslational modifications of the proteins are taken into account. Dynamic posttranslational modification of proteins is often crucial for the preservation and regulation of the protein structure and function. At present, several hundred different posttranslational modifications of proteins are known, of which phosphorylation is by far the most prominent. Enzymatically catalysed phosphorylation and dephosphorylation is an important regulatory element for the living cell. Organisms utilise reversible protein phosphorylation for control of such fundamental cellular processes as signal transduction, cell cycle, organisation of the cytoskeleton, metabolism and programmed cell death and gene expression. Transient and reversible phosphorylation of certain amino acids of corresponding proteins involved in these processes serves for stringent control of activity, stability, localisation or interactions. A comprehensive analysis of phosphoproteins and the determination of phosphorylation sites is accordingly the prerequisite for understanding of complex biological systems and the molecular bases for the development of diseases.

However, the very proteins involved in regulatory processes are generally only represented in the cell in relatively low abundance. In addition, transient phosphorylation of proteins is rarely stoichiometric, and consequently the phosphorylated species generally occurs together with the unphosphorylated form. The analysis and identification of phosphoproteins and the identification of phosphorylation sites must in addition generally be carried out by sensitive mass-spectrometric methods owing to the small amounts available. These methods typically require enzymatic cleavage of the phosphoprotein to be analysed into fragments, usually into tryptic peptides. However, phosphorylated amino acids only occur in certain peptides, which contain recognition sequences for the enzymes involved in the phosphorylation. Besides the stoichiometric effects mentioned above, phosphopeptides are therefore themselves in the form of a mixture with unphosphorylated peptides of the same protein in the case of analysis of a phosphoprotein purified to homogeneity. In an analysis, peptides can no longer be detected reliably below a certain relative abundance in the peptide mixture. Firstly, weak, small signals may disappear in the background noise, and secondly highly abundant peptides compete for the ionisation energy, meaning that peptides of low abundance may possibly not be ionised at all, and thus also not detected, without prior enrichment. It is estimated that about 100,000 potential phosphorylation sites in the primary sequence of corresponding proteins in the human proteome are encoded, but to date it has only been possible to identify about 2000 of these. Strategies for the selective and efficient enrichment of phosphorylated peptides from proteolytic extracts of phosphorylated proteins with high yield are accordingly an integral part of comprehensive analysis of the phosphoproteome.

Owing to the often low abundance of phosphoproteins and the substoichiometric occurrence of phosphorylation of the corresponding amino acids, a reproducible enrichment method for phosphorylated peptides for the analysis of the phosphoproteome must give the most quantitative yield possible of the corresponding phosphopeptide here in order also to enable analysis of phosphopeptides of low abundance. At the same time, the enrichment method must provide quantitative purity in order to allow direct analysis of the phosphopeptides in the sample in spite of the stoichiometric effects mentioned above.

It is estimated that one third of all proteins present in a typical mammal cell can potentially be modified posttranslationally by phosphorylation. The enzymes responsible for this, the kinases, represent about 1-3% of the expressed genome of a typical mammal cell. The modification of the protein by phosphorylation can occur here in the side chains of the amino acids serine, threonine, tyrosine, histidine, arginine, lysine, cysteine, glutamate and aspartate. However, the three amino acids serine (about 90%), threonine (about 10%) and tyrosine (about 0.05%) are the preferred residues. Methods for the enrichment of phosphorylated peptides should accordingly be applicable to an equal extent to the phosphorylated derivatives of at least the three amino acids serine, threonine and tyrosine.

Traditional methods for the analysis of phosphorylation sites in proteins use the possibility of employing radioactive phosphorus isotopes ($[P^{32}]$, $[P^{33}]$) for labelling phosphoproteins in order subsequently to analyse the sample in accordance with the prior art by gel electrophoresis, enzymatic digestion and sequencing or peptide mapping. In order to determine quantitative differences within the phosphoproteome of two different cell states, the intensity of the radioactive radiation of two samples is compared with one another. The disadvantages of a method of this type are firstly the use of radioactive radiation per se and the resultant contamination of, for example, measuring instruments. In addition, only metabolism-active samples can be employed for this method. Non-metabolism-active, clinically relevant samples, such as, for example, tissue biopsies from cancer patients, cannot be analysed using this method. In addition, phosphoproteins have different reaction rates for enzyme-catalysed phosphorylation, meaning that quantitative results regarding the correlation between the abundance of the protein and the incorporation rate of $[P^{32}]$ or $[P^{33}]$ may be inaccurate. A quantitative yield and purity in the sense of the present invention thus cannot be achieved by labelling phosphoproteins with radioactive phosphorus isotopes in accordance with the prior art.

A further method for the enrichment of phosphoproteins is affinity enrichment by means of phospho-specific antibodies. To this end, use is made of antibodies which bind specifically to phosphoaminoepitopes of phosphoserine, -threonine or -tyrosine. However, specific antibodies have not yet been found for all epitopes of phosphoamino acids. Antibodies, in particular those directed against phosphoserine and -threonine, are frequently unable to react with the phosphorylated amino acids owing to steric hindrance. If certain phosphoproteins are only bound with low affinity by the antibodies employed, the high proportion of nonspecific binding of other, unphosphorylated proteins may prevent analysis of the phosphorylation sites of the protein.

Immune affinity enrichment of phosphoproteins or -peptides in accordance with the prior art is thus subject to a number of limitations. It is thus not possible to achieve a quantitative yield and purity using this method.

An indirect method for the enrichment of proteins/peptides using phosphoserine and -threonine is chemical conversion of the phosphate groups of the protein or peptides The groups are chemically modified here and provided with affinity tags, for example biotin, or covalently immobilised for enrichment. The disadvantage of these methods is the occurrence of side reactions during the chemical modification, meaning that, for example, undesired modification of amino acids or nonspecific fragmentation of proteins and peptides occurs, making identification of the peptides in the mass spectrum more difficult. In addition, multistep chemical modifications are complex to carry out and usually require relatively large amounts of sample.

A further method for the enrichment of phosphorylated peptides from complex mixtures is immobilised metal chelate affinity chromatography (IMAC). The enrichment of phosphopeptides by IMAC is simple to carry out, in principle requires no modification of the samples before the enrichment, can be used for non-metabolism-active samples, does not distinguish between different phosphoamino acids and in addition is relatively inexpensive to carry out. For this reason, IMAC is currently the most advantageous method for the isolation of phosphopeptides.

IMAC is carried out in accordance with the prior art with the aid of chromatography materials which have been surface-modified with chelating agents for the binding of metal ions [summarised in Gaberc-Porekar V. and Menart V. (2001): "Perspectives of immobilised-metal affinity chromatography" *J. Biochem. Biophys. Methods*, 49, 335-360]. For phosphopeptide enrichment, surface modifications by iminodiacetate (IDA), a tridentate chelating agent [Porath J. and Olin B (1983): "Immobilised metal ion affinity adsorption and immobilised metal ion affinity chromatography of biomaterials" *Biochemistry* 22, 1621-1630], and nitrilotriacetate (NTA), a tetradentate chelating agent [Hochuli E., Doebeli H and Schacher A (1987): "New metal chelate adsorbent selectivity for proteins and peptides containing neighbouring histidine residues" *J. Chrom.*, 411, 177-184], and IPAC (immobilised phosphonic acid chelating) [Kaffashan A. and Zeng C. (2003). "Evaluation of commercially available IMAC Kits: Millipore ZipTip$_{MC}$, IPAC beads and Pierce Swell Gel Gallium Chelated disks" Poster presented at the 51st ASMS Conference on Mass Spectrometry and Allied Topics, 2003, Montreal, Canada], are described. Besides their efficiency in the enrichment of phosphopeptides, the accessibility of the ligands must also be considered. Most ligands are only accessible in multistep reactions and are thus expensive and complex to prepare. Support materials having ligands which not only enable effective enrichment, but can also be prepared simply and quickly and thus inexpensively would therefore be desirable.

The efficiency of IMAC, i.e. the purity and yield of the isolated phosphopeptides, is determined principally by the following factors besides the choice of a suitable support material and ligands,:

1. Choice of the buffer conditions during binding
2. Choice of the buffer conditions during elution
3. Choice of the metal ion for activation of the chelate ligands Regarding 1:

A contribution to the binding of a phosphopeptide to immobilised metal ions is made by all electron donors present in polypeptides, in particular the side chain of histidine, but also other basic amino acids and acidic amino acids, such as glutamate and aspartate, and the phosphate group on the side chain of phosphorylated amino acids. It can thus be expected that the selectivity of IMAC for phosphopeptides is problematic with respect to the desired purity of the phosphopeptide before the analysis. In accordance with the prior art, the binding of phosphopeptides to immobilised metal ions is therefore carried out at acidic pH (2.5 to 3.5) in order to obtain higher specificity with respect to phosphopeptides by protonation of the side chains of the basic amino acids. However, the affinity to immobilised metals, which is promoted by the carboxyl group of acidic amino acids, is not restricted thereby. Nonspecific binding of acidic peptides to immobilised metal ions is accordingly also the main problem of IMAC carried out in accordance with the prior art for the enrichment of phosphopeptides [Kalume D. E., Molina H. and Pandey A. (2003). "Tackling the phosphoproteome: tools and strategies" *Current Opinion in Chemical Biology*, 7, 64-69].

Regarding 2:

A further point in the IMAC of phosphopeptides is quantitative elution of the bound phosphopeptides from the immobilised metal ions. For the elution of phosphopeptides, the prior art describes various bases, such as NaOH, NH$_4$OH or 0.1 M carbonate, or competitive elution by phosphate ions at pH 8.4 to 9.4 in combination with an organic polymer as support material [Heintz et al., Electrophoresis 2004, 25, 1149-1159]. However, quantitative elution of the bound phosphopeptides is not possible using these methods.

Regarding 3:

In accordance with the prior art, the enrichment of phosphorylated peptides by IMAC can be carried out using various ions of the transition metals and trivalent metal ions from the third main group, which vary with respect to their efficiency and selectivity, depending on the other isolation conditions (for example ligand, binding and elution conditions). Suitable ions mentioned are, for example, gallium(III), iron(III), aluminium(III) and zirconium(IV).

In spite of intensive research work, however, it has to date not been possible to develop a method which allows a quantitative yield at the same time as quantitative purity.

The object of the present invention was therefore to develop a method for the isolation of phosphopeptides which enables virtually quantitative isolation at the same time as high purity of the products.

It has been found that the use of support materials based on silica in combination with certain basic elution buffers enables particularly efficient isolation of phosphopeptides.

Particularly high efficiency is evident on use of a novel support material having chelate ligands based on ethylenediaminediacetic acid.

The present invention relates to a method for the enrichment of phosphopeptides, characterised by the following method steps:
a) provision of a support material having chelate ligands based on silica
b) activation of the support material from step a) using transition-metal ions, oxides or oxide hydrates of transition-metal ions or trivalent ions of metals from the third main group
c) bringing a phosphopeptide-containing sample into contact with the activated support material in the presence of a binding buffer
d) removal of the supernatant consisting of the binding buffer and the unbound part of the sample
e) optionally washing of the support material
f) elution of the phosphopeptides with an elution buffer which has a pH>10 and comprises alkali metal, alkaline earth metal or ammonium salts of thiocyanate, of acids of the complex ligands nitrito, isocyano, nitrile, isocyanato, isothiocyanato, azido, ethylenediamine, isonitrile, fulminato and cyano and/or of the oxygen acids of phosphorus, sulfur, vanadium, ruthenium, niobium, tantalum, tungsten or of molybdenum, and/or chelating agents, such as EDTA, EGTA or salicylic acid.

In a preferred embodiment, the activation in step b) is carried out using iron(III) ions, particularly preferably using zirconium(IV) ions.

In a preferred embodiment, the elution in step f) is carried out with an elution buffer which comprises alkali metal, alkaline earth metal or ammonium salts of oxygen acids of phosphorus or particularly preferably of thiocyanate in a concentration of between 0.005 and 2 mol/l.

In a further preferred embodiment, the phosphopeptides eluted in step f) are investigated directly, i.e. directly after desalination or preferably directly without desalination, by mass spectrometry, thin-layer chromatography or by sequence analysis.

In a preferred embodiment, a, support material having chelate ligands of the formula Ia and/or Ib is provided in step a)

$m=2$ to 8, where one or more non-adjacent C atoms may be replaced by O, NH, S or —C=C—.

In a particularly preferred embodiment, a support material having a chelate ligand which consists of magnetite particles whose surface is at least partly covered by silica is provided in step a).

The present invention furthermore relates to a kit for the enrichment of phosphopeptides, at least containing a support material having a chelate ligand based on silica and an elution buffer which has a pH>10 and comprises alkali metal, alkaline earth metal or ammonium salts of thiocyanate, of acids of the complex ligands nitrito, isocyano, nitrile, isocyanato, isothiocyanato, azido, ethylenediamine, isonitrile, fulminato or cyano and/or of the oxygen acids of phosphorus, sulfur, vanadium, ruthenium, niobium, tantalum, tungsten and/or molybdenum and/or chelating agents, such as EDTA, EGTA or salicylic acid.

In a preferred embodiment, the support material having a chelate ligand has been activated using iron(III) or preferably zirconium(IV) ions.

In a preferred embodiment, the kit contains, as support material, magnetite particles which are at least partly coated with silica.

In another preferred embodiment, the kit contains a support material having chelate ligands conforming to the formula Ia and/or Ib, where R=methyl and m=2.

In a further preferred embodiment, the kit contains, as elution buffer, a buffer which comprises alkali metal, alkaline earth metal or ammonium salts of oxygen acids of phosphorus or particularly preferably of thiocyanate in a concentration of between 0.005 and 2 mol/l.

The present invention also relates to a support material, characterised in that it contains chelate ligands of the formula Ia and/or Ib

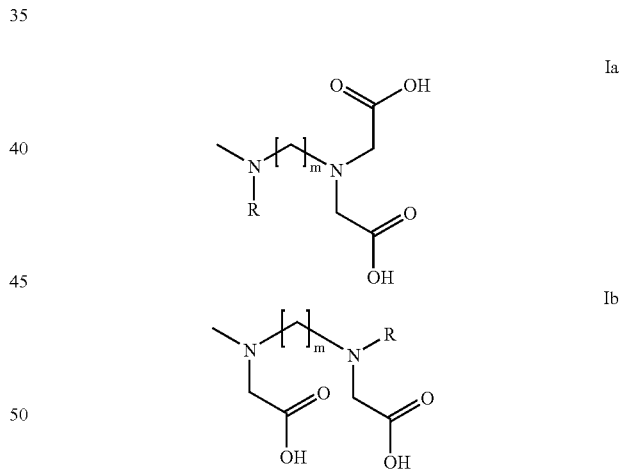

where
R=C1 to C6 alkyl or C5 to C18 aryl, optionally mono- or polysubstituted, for example by hydroxyl, C1-C4-alkoxy, amino, alkylamino, CN or halogen radicals,
$m=2$ to 8, where one or more non-adjacent C atoms may be replaced by O, NH, S or —C=C—.

In a preferred embodiment, R is ethyl, particularly preferably methyl.

In a preferred embodiment, $m=2$.

Figure 1:
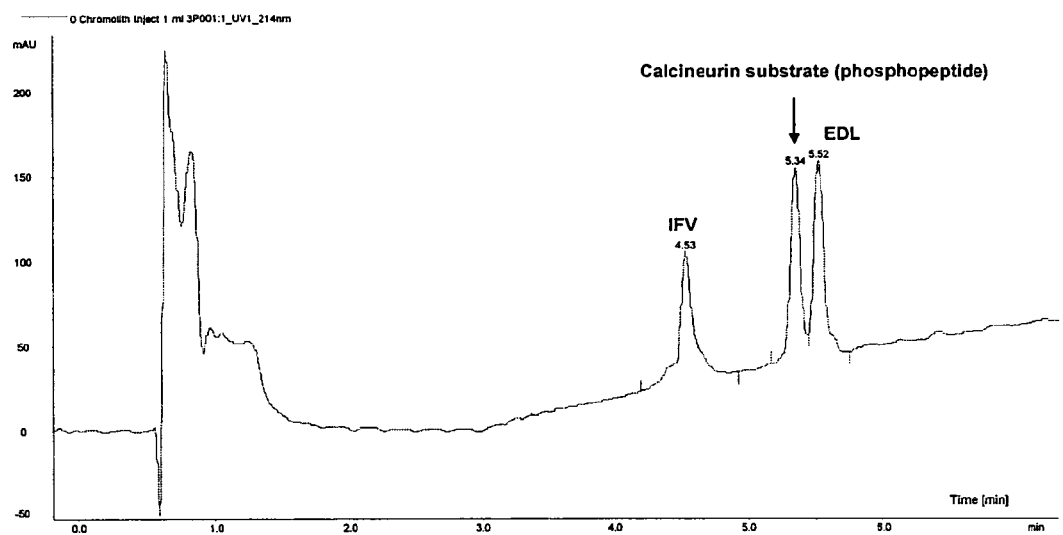
FIG. 1 shows an HPLC chromatogram with the peaks of the three model peptides for the simultaneous qualitative and quantitative analysis of methods for phosphopeptide enrichment by IMAC. Further details are given in Example 1.

In accordance with the invention, phosphopeptides are peptides, polypeptides or proteins which have been phosphorylated at at least one site. The length of the phosphopeptides is not crucial. The only important point is that the peptides are soluble under the conditions employed for the enrichment (i.e. typically in the binding buffers). In general, it is therefore possible to employ peptides which are soluble at a pH of about 2.5. The solubility can be supported here by addition of chaotropic substances. The length of the peptides is typically in the length ranges as obtained after enzymatic or chemical cleavage, for example a tryptic digestion. However, it is just as possible to enrich shorter or longer phosphopeptides using the method according to the invention.

A phosphopeptide-containing sample is a solution in which phosphopeptides are present or at least assumed. The phosphopeptide-containing sample is usually the solution obtained after chemical or enzymatic cleavage.

Support materials are solid materials as typically employed for chromatographic or extraction purposes. Support materials based on silica are materials which consist entirely of glass, ceramics and/or silica or in which the surface is at least partly covered by glass, ceramics and/or silica. The term silica also encompasses materials prepared using silanes carrying one or two organic radicals (i.e., for example, C1 to C8-alkyl and/or C5 to C18 aryl radicals, in particular methyl, ethyl, n/iso-propyl, n/tert-butyl, phenyl, benzyl or naphthyl), i.e. so-called hybrid materials.

The support material can be, for example, in the form of a monolithic column, plate, particle, coating, fibre, filter or other porous or nonporous structure. The material is preferably in the form of a particle. Preference is given in accordance with the invention to the use of silica materials.

The support material particularly preferably consists of magnetite particles which are at least partly coated with silica.

Various production processes are known for the production of magnetite particles. Examples are disclosed in:

Massart, IEEE Trans. Magn. 17, 1247-1248 (1981)
Sugimoto, Matijevic, J. Colloid Interface Sci. 74, 227-243 (1980)
Qu et al., J. Colloid Interface Sci. 215, 190-192 (1999)

The magnetite solid phase is particularly preferably produced by the method of Sugimoto and Matijevic.

A further advantage of magnetic materials is their simple removal from liquid media by application of a magnetic field.

An example of a support material comprising magnetite particles whose surface is covered by silica and which is particularly suitable in accordance with the invention is Mag-Prep® Silica particles from Merck KGaA, Germany. An example of silica particles which are suitable in accordance with the invention are LiChrospher® particles from Merck KGaA, Germany.

A support material having a chelate ligand is a support material to which chelate ligands are covalently bonded.

Support materials having a chelate ligand which are suitable in accordance with the invention are support materials based on silica to which tridentate, tetradentate or pentadentate metal chelate ligands are covalently bonded. Suitable tridentate, tetradentate or pentadentate chelate ligands are known to the person skilled in the art in the area of IMAC. Examples are iminodiacetate (IDA), a tridentate chelating agent, and the tetradentate chelating agent nitrilotriacetate (NTA) or IPAC (immobilised phosphonic acid chelating).

In accordance with the invention, particular preference is given to the use of a support material having a chelate ligand based on ethylenediamine diacetate. This support material having a chelate ligand is produced by reaction of an activated support material with correspondingly functionalised ligands based on ethylenediamine diacetate.

In accordance with the invention, activated support materials is taken to mean support materials having reactive groups which are able to undergo covalent bonding to primary and/or secondary amines with or without addition of additional reagents. Corresponding activated support materials are also used, for example, for the introduction of separation effectors into support materials for chromatography. Examples of activated support materials are materials having azlactone groups or NHS esters, and preferably support materials having epoxide groups. The person skilled in the art is aware what reaction conditions and/or additional reagents are necessary to produce a covalent bond of the alkylenediamine of the formula II to a specific activated support. For the preparation of the support materials according to the invention having a chelate ligand based on ethylenediamine diacetate, an activated support material, preferably epoxide-activated support material, is reacted with the amino-functionalised ligands of the formula II

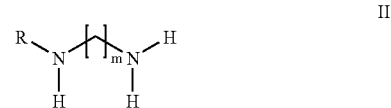

II in which R=C1 to C6 alkyl or C5 to C18 aryl, optionally mono- or polysubstituted, for example by hydroxyl, C1-C4-alkoxy, amino, alkylamino, CN or halogen radicals, m=2 to 8, where one or more non-adjacent C atoms may be replaced by O, NH, S or —C≡C—.

The modified support material is subsequently reacted with monohaloacetic acid. Since the aim is to obtain a tetradentate ligand, this reaction is generally carried out with at least two equivalents of haloacetic acid per ligand. The haloacetic acid used is preferably bromoacetic acid.

Figure 7:
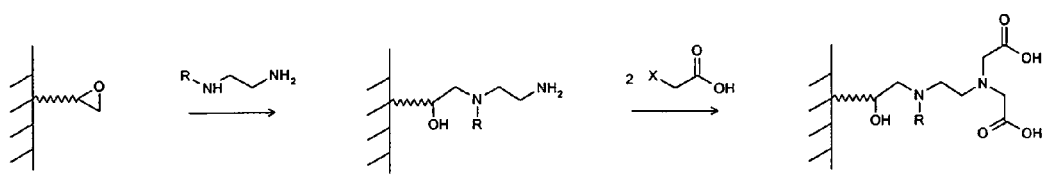
FIG. 7 shows by way of example the synthesis of a support material having a chelate ligand based on ethylenediamine diacetate which is preferred in accordance with the invention.

FIG. 7 shows diagrammatically the synthesis of a support material having chelate ligands according to the invention starting from an epoxy-activated support material. R here has the meaning as in formula Ia/b and X=Cl, Br or I. For reasons of clarity, only the synthesis of one ligand of the formula Ia is shown. It goes without saying that not only—as shown in the reaction scheme—one ligand, but instead a multiplicity of ligands is bonded to the support material in the reaction. The number of ligands per amount unit of support material depends on the number of reactive groups on the support material which are available for bonding of the ligands.

Due to the simple and rapid preparation, the support material according to the invention having a chelate ligand based on ethylenediamine diacetate offers a further advantage in addition to its good properties in IMAC, since many other ligands are only accessible by means of very complex and long syntheses.

The support materials according to the invention having a chelate ligand based on ethylenediamine diacetate carry ligands of the formula Ia and/or Ib since in the first step of the synthesis, both the primary and also the secondary amino group of the compound of the formula II is able to react with the activated support material. The ratio in which the two amino groups react and the ratio in which structures of the formula Ia and Ib are thereby formed depends, inter alia, on the steric and electronic influence of the radical R in formula II. However, it should be assumed that support materials are generally formed in which some of the ligands have the formula Ia and some of the ligands have the formula Ib

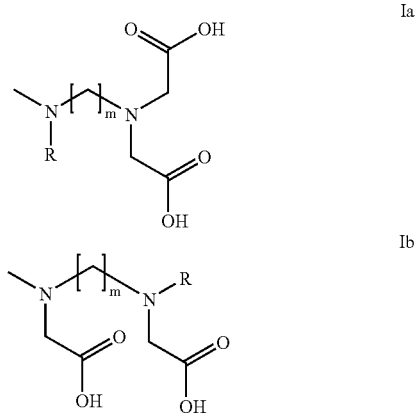

where
R=C1 to C6 alkyl or C5 to C18 aryl, optionally mono- or polysubstituted, for example by hydroxyl, C1-C4-alkoxy, amino, alkylamino, CN or halogen radicals,
m=2 to 8, where one or more non-adjacent C atoms may be replaced by O, NH, S or —C≡C—.

Particular preference is given to support materials having ligands of the formula Ia and/or Ib in which m=2. Preference is furthermore given to support materials having ligands of the formula Ia and/or Ib in which R is a short-chain, wherever possible small radical, such as R=ethyl, methyl, hydroxyethyl or trifluoromethyl. Particular preference is given to the support material having ligands where m=2 and R=ethyl or methyl, in particular R=methyl. Support materials which carry chelate ligands where m=2 and R=ethyl are referred to below as ethyl-EDDA-modified support materials. Support materials which carry chelate ligands where m=2 and R=methyl are referred to as methyl-EDDA-modified support materials.

The support materials according to the invention having chelate ligands based on ethylenediamine diacetate are suitable for all applications in which conventionally immobilised chelate ligands are employed. They are particularly suitable for biochromatography of proteins or peptides, very particularly for the enrichment of phosphopeptides. For applications other than the enrichment of phosphopeptides, other support materials, such as organic polymers or other inorganic oxides, besides the support materials based on silica can also be employed for the preparation of the support materials according to the invention having a chelate ligand based on ethylenediamine diacetate.

The efficiency of IMAC of phosphopeptides is determined by the quantitative yield of the enrichment and by the quantitative purity of the isolated phosphopeptides. The most quantitative yield possible of the corresponding phosphopeptides at the same time as quantitative purity is desirable. For the purposes of the invention, quantitative yield denotes a yield of phosphopeptide of 80%, preferably of 90% or more. For the purposes of the invention, quantitative purity denotes a purity of phosphopeptide of 80%, preferably of 90% or more.

In order to determine the efficiency of an enrichment, i.e. simultaneously the quantitative yield and qualitative purity of the product, a test method has been established. This test method is based on the different retention behaviour of peptides in reversed-phase (RP) HPLC separation and the associated possibility of direct quantification of the amount of peptide present in a sample solution in relation to a calibration standard by integration of the UV absorption signal. Further details on this test are given in Example 1.

With the aid of the method according to the invention, it is possible for the first time to achieve enrichment of phosphopeptides with quantitative yield at the same time as virtually complete purity.

It is also important that the method according to the invention additionally
  makes no distinction between different phosphoamino acids
  allows direct analysis of the isolated phosphopeptides
  is simple to carry out
  works wherever possible without sample modification, i.e. avoids complex reaction sequences for the chemical modification of peptide mixtures and the associated problems with respect to reproducibility and the amount of sample to be employed, and
  can also be used for non-metabolism-active samples in order to enable the analysis of clinically relevant samples, such as, for example, tissue from biopsies.

The efficiency of the enrichment of phosphopeptides by means of IMAC is generally influenced, in particular, by the following parameters:
  choice of the support material
  choice of the chelate ligand
  choice of the metal ions for activation of the chelate ligand
  the buffer conditions during bonding of the phosphopeptides
  the buffer conditions during elution of the phosphopeptides It has now been found that a specific choice of these parameters gives rise to particularly efficient enrichment with respect to yield and purity of the product. For this reason, firstly the individual method steps are given below in a general manner and subsequently the respective parameters are discussed.

For the isolation of phosphopeptides by means of IMAC, the following method steps are typically carried out:
  a) provision of a support material having a chelate ligand
  b) activation of the chelate ligand with the aid of metal ions
  c) addition of the phosphopeptide-containing sample to the support material in the presence of a binding buffer (the binding buffer may be mixed in advance with the sample and/or the support material. Equally, the binding buffer may already be added to the support material in step b))

d) removal of the supernatant consisting of binding buffer and unbound fraction of the sample
e) optionally washing of the support material containing the bound phosphopeptides
f) elution of the bound phosphopeptides from the support material The eluted phosphopeptides can then be sent for any suitable analysis. Particularly suitable methods are chromatographic methods, such as thin-layer chromatography, sequencing methods and/or spectrometric methods, such as, in particular, MALDI or ESI mass spectrometry. To this end, the samples can be sent for analysis directly or after prior desalination. Removal of the salts of the elution buffer may be necessary since some analytical methods, in particular mass-spectrometric methods, such as MALDI-mass spectrometry, are disrupted by the presence of salts. A possible desalination method is, for example, reversed-phase chromatography.

It has been found that on use of the elution buffer based on thiocyanate salts which is preferred in accordance with the invention, the sample can be analysed directly by means of MALDI-mass spectrometry without prior desalination and nevertheless excellent analytical sensitivities are achieved. This was not possible with the elution buffers known to date at the same time as a high phosphopeptide yield.

Discussion of the Individual Parameters

Activation of the Chelate Ligands

The chelate ligands of the support material are activated using transition-metal ions, oxides and oxide hydrates of transition metals or trivalent ions of metals from the third main group. Preference is given to activation using iron(III) ions, particularly preferably using zirconium(IV) ions. To this end, the support material having chelate ligands is incubated in aqueous solutions of the corresponding metal salts. The concentration of the solutions is typically between 1 and 500 mmol/l. The duration of the incubation is typically between 1 minute and 12 hours. Examples of suitable salts are $MnCl_2$, $NiCl_2$, $CuCl_2$, $GaCl_3$ and in particular $FeCl_3$ and $ZrOCl_2$.

Binding Buffer

The binding buffer employed can be any binding buffer known in accordance with the prior art for the IMAC of phosphopeptides. Examples thereof are 0.005 to 20% acetic acid or formic acid in water. The binding buffer employed in accordance with the invention is preferably 1.5% acetic acid or formic acid in water.

Wash Buffer

The wash buffer employed can be any wash buffer known in accordance with the prior art for the IMAC of phosphopeptides. Examples thereof are 0.001 to 2% acetic acid or formic acid in water. The wash buffer employed in accordance with the invention is preferably 0.1% acetic acid or formic acid in water. Two or more washing steps are preferably carried out, where a purely aqueous wash buffer is used in the first step, and a wash buffer which comprises an organic solvent, such as, for example, acetonitrile or methanol, is used in the next step.

Elution Buffer

In accordance with the invention, the phosphopeptides are eluted from the support with elution buffers which have a pH>10, preferably a pH of about 10.5, and comprise at least one or more of the following components:
  alkali metal, alkaline earth metal or ammonium salts of thiocyanate
  alkali metal, alkaline earth metal or ammonium salts of acids of the complex ligands nitrito, isocyano, nitrile, isocyanato, isothiocyanato, azido, ethylenediamine, isonitrile, fulminato and/or cyano,
  alkali metal, alkaline earth metal or ammonium salts of oxygen acids of phosphorus, sulfur, vanadium, ruthenium, niobium, tantalum, tungsten and/or of molybdenum
  chelating agents, such as EDTA, EGTA or salicylic acid.

Surprisingly, it has been found that the yield of the elution of the phosphopeptides from silica supports having chelate ligands according to the invention which are activated using metal ions can be significantly increased if elution buffers of strongly alkaline pH are employed. The elution according to the invention of phosphopeptides with sodium and ammonium salts of oxygen acids of phosphorus at pH>10 has enabled significantly higher yields to be achieved than in accordance with the prior art, for example in the case of the use of both iron(III), gallium(III) and zirconium(IV).

In accordance with the invention, preference is given to elution with elution buffers which comprise alkali metal, alkaline earth metal and/or ammonium salts of oxygen acids of phosphorus.

It has furthermore been found that particularly effective elution is achieved with alkali metal, alkaline earth metal and ammonium salts of thiocyanate, and these eluates can be investigated particularly well directly without further purification by mass spectrometry. In accordance with the invention, particularly preferred elution buffers therefore comprise alkali metal, alkaline earth metal and/or ammonium salts of thiocyanate.

The concentration range of the salts in the elution buffers is typically between 0.005 and 2 mol/l. Preference is given to concentrations of between 50 and 200 mM, particularly about 100 mM.

The present invention also relates to a kit for the enrichment of phosphopeptides, at least containing a support material having chelate ligands based on silica and an elution buffer which has a pH>10, particularly preferably a pH of about 10.5, and comprises at least one or more of the following components:
  alkali metal, alkaline earth metal or ammonium salts of thiocyanate
  alkali metal, alkaline earth metal or ammonium salts of acids of the complex ligands nitrito, isocyano, nitrile, isocyanato, isothiocyanato, azido, ethylenediamine, isonitrile, fulminato and/or cyano
  alkali metal, alkaline earth metal or ammonium salts of oxygen acids of phosphorus, sulfur, vanadium, ruthenium, niobium, tantalum, tungsten and/or of molybdenum
  chelating agents, such as EDTA, EGTA or salicylic acid.

The support material here can be in activated or non-activated form. The support material is preferably in the form of an aqueous suspension in iron(III) or zirconium(IV) ion-activated form.

In a preferred embodiment, the kit additionally contains further constituents, such as preferably binding and/or wash buffers. It may furthermore contain further constituents, such as, for example, reagents for activation of the support material.

In a particularly preferred embodiment, the kit contains a zirconium(IV) ion-activated support material in the form of magnetite particles which are at least partly coated with silica and carry chelate ligands of the formula Ia and/or Ib where R=methyl and m=2.

In a further preferred embodiment, the kit contains, as elution buffer, a buffer comprising 0.005 to 2 mol/l of ammonium thiocyanate and having a pH>10, particularly preferably having a pH of about 10.5.

Even without further comments, it is assumed that a person skilled in the art will be able to utilise the above description in the broadest scope. The preferred embodiments and examples should therefore merely be regarded as descriptive disclosure which is absolutely not limiting in any way.

The complete disclosure content of all applications, patents and publications mentioned above and below, in particular the corresponding application EP 04011468.8, filed on 14 May 2004, is incorporated into this application by way of reference.

EXAMPLES

1. Chromatographic Separation of Three Peptides for Determination of the Yield and Purity of the Purification For this test, a model peptide mixture of low complexity comprising three peptides which are sufficiently different in retention behaviour was used. One of these peptides is basic, one is acidic and a third is a monophosphopeptide. The characteristics of the peptides are shown in Table 1.

TABLE 1

Characteristics of the model peptides for quantitative and qualitative analysis of methods for phosphopeptide enrichment Peptide 2 is the only phosphopeptide employed besides a basic phosphopeptide (peptide 1) and an acidic phosphopeptide (peptide 3).

| Peptide | Amino acid sequence | Molecular weight | pH |
|---|---|---|---|
| 1 | IFVQKCAQCHTVEK | 1633.94 g/mol | 8.06 |
| 2 | DLDVPIPGRFDRRVpSVAAE | 2192.40 g/mol | 4.93 |
| 3 | EDLIAYLK | 964.13 g/mol | 4.37 |

The test thus allows the investigation of the separation of acidic and basic peptides from a phosphopeptide present in the mixture with the aid of a directly quantifiable signal.

FIG. 1 shows a typical RP-HPLC profile of the separation of the model peptide mixture. All signals are sufficiently separated, which allows clear integration of the corresponding UV signals. Taking into account the standard deviation in the order of a maximum of 0.05 min or 3 s, the net retention times of the individual peptides (see Table 2) are in addition sufficiently different and reproducible that clear assignment of the peptides in chromatograms of extensive experimental series is possible. If the model peptides are measured as calibration standards, the areas of these peaks correspond 100% to the calculation of yield and purity of the phosphopeptide.

TABLE 2

The retention times of the model peptides are sufficiently different and reproducible to allow clear assignment and integration of the signals. The table shows the means of the retention times of the model peptides from three measurements carried out independently of one another.

| Peptide | Net retention time [min] | | | Mean [min] | Standard deviation [min] |
|---|---|---|---|---|---|
| 1 | 4.53 | 4.55 | 4.47 | 4.52 | 0.04 |
| 2 | 5.34 | 5.25 | 5.25 | 5.28 | 0.05 |
| 3 | 5.42 | 5.51 | 5.43 | 5.45 | 0.05 |

The separations are carried out on a Chromolith® Performance RP 18e column connected to an ÄKTA Explorer chromatography unit. A linear gradient from acetonitrile to water against a background of 0.1% TFA at a flow rate of 3 ml/min is employed. The eluents are A: water comprising 0.1% of TFA and B: 80% acetonitrile and 0.1% TFA in water.

| Equilibration: | 6 ml at 5% B |
|---|---|
| Gradient: | 5-100% B during increase by 9.5% B/min subsequently reduction to 5% B in 1 min |
| Re-equilibration: | 6 ml at 5% B |

2. Synthesis of the Support Materials having a Chelate Ligand according to the Invention 1. Production of Epoxy-Modified Magnetic Silica Particles:

5 g of MagPrep® silica HS particles (Merck KGaA, Germany) are repeatedly washed salt-free with deionised water and subsequently suspended in 100 ml of deionised water. The suspension is stirred in a three-necked flask fitted with precision glass stirrer, reflux condenser and dropping funnel. 0.01 mol of sodium acetate is dissolved in the magnetic particle suspension. 1.25 g of glycidyloxypropyltrimethoxysilane, dissolved in 8.3 ml of isopropanol, are subsequently added dropwise over the course of 15 min. The mixture is heated to 80° C. and stirred at this temperature for 3 h. After cooling, the magnetic particles are washed 5 times with 100 ml of deionised water each time. If the particles are to be immediately reacted further, they can remain in the aqueous suspension. Otherwise, they are repeatedly washed with acetone until free from water and then dried for 1.5 h under reduced pressure at 50° C.

2. Production of IDA-Modified Magnetic Silica Particles:

1.5 g of iminodiacetic acid and 0.8 g of sodium acetate are dissolved in 100 ml of a 5% suspension of the epoxy-activated particles produced in accordance with step 1. The pH is adjusted to 9 using a few drops of dilute sodium hydroxide solution, and the mixture is stirred for 1 h at 70° C. After cooling, the particles are washed 5 times with 100 ml of deionised water each time. They are stored as a 5% suspension in deionised water.

3. Production of Methyl-EDDA-Modified Magnetic Silica Particles:

100 ml of a 5% aqueous suspension of the epoxy-activated particles produced in accordance with step 1 are stirred with 2.65 g of N-methyl-ethylenediamine in the apparatus described above for 1 h at 65° C. After cooling, the particles are washed 5 times with 100 ml of deionised water each time. 5.5 g of bromoacetic acid are dissolved in the resultant suspension (100 ml). After addition of about 0.8 g of sodium acetate, the pH is adjusted to 8 using dilute NaOH, and the suspension is stirred overnight at room temperature. The particles are subsequently washed a number of times with deionised water.

4. Production of Ethyl-EDDA-Modified Magnetic Silica Particles:

The production is carried out analogously to step 3, but with 3.15 g of N-ethylethylenediamine.

5. Production of Hydroxyethyl-EDDA-Modified Magnetic Silica Particles:

3.12 g of 2-(2-aminoethylamino)ethanol are made up to 25 ml (about 1M) with deionised water. The solution is adjusted to pH 10 using HCl. 1 g of acetone-dried epoxy-activated particles is suspended in this solution. The mixture is shaken for 7 h at room temperature, subsequently washed five times with deionised water and dried for 1.5 h at 50° C. under reduced pressure.

6. Production of Epoxy-Modified Silica Particles:

50 g of LiChrospher® Si 300, 15-40 µm particles (Merck KGaA, Germany) are suspended in 600 ml of 0.1 molar sodium acetate solution. The suspension is stirred in a three-necked flask fitted with precision glass stirrer, reflux condenser and dropping funnel. 80 g of glycidyloxypropyltrimethoxysilane, dissolved in 400 ml of isopropanol, are subsequently added dropwise over the course of 25 min. The mixture is heated to 80° C. and stirred at this temperature for 2 h. After cooling, the silica gel is filtered off with suction through a glass filter frit and washed firstly 5 times with 200 ml of deionised water each time, then twice with 200 ml of isopropanol each time. The material is dried for 24 h at 50° C. under reduced pressure.

7. Production of Methyl-EDDA-Modified Silica Particles:

25 g of the epoxy-activated silica gel particles produced in accordance with Example 6 are suspended in 300 ml of deionised water and stirred for 1.5 h at 65° C. with 75 ml of N-methylethylenediamine in the apparatus described above. After cooling, the silica gel is filtered off with suction through a glass filter frit and washed 5 times with 200 ml of deionised water each time. The moist silica gel is subsequently resuspended in 600 ml of 0.1 molar sodium acetate solution. 17.6 g of bromoacetic acid are added, and the pH of the suspension is adjusted to 8.7 using 10% sodium hydroxide solution. The mixture is stirred for 20 h at room temperature. The silica gel is subsequently filtered off with suction through a glass filter frit and rinsed a number of times with deionised water.

8. Activation of the Chelate-Modified Particles Using Metal Ions:

5 mmol of metal salt (for example $MnCl_2$, $NiCl_2$, $FeCl_3$, $CuCl_2$, $GaCl_3$, $ZrOCl_2$) are dissolved in 20 ml of deionised water. The pH is, if necessary, adjusted to 7 by addition of a few drops of dilute sodium hydroxide solution or hydrochloric acid. The solution is subsequently mixed with a suspension of 1 g of chelate-modified particles (production corresponding to steps 2-5 and 7) in 20 ml of deionised water and shaken for 1 h at room temperature. The particles are washed ten times with deionised water and stored as a 5% aqueous suspension.

3. Protocol for Carrying out the Enrichment Method according to the Invention

In its preferred embodiment, the method according to the invention for the isolation of phosphopeptides is carried out in accordance with the following protocol. The general method parameters, i.e. the sequence of the method steps, their duration, etc., can also be applied to the performance of the method according to the invention with other reagents (for example activation using other metal ions, use of other buffers or support materials).

As support material, use is made of magnetic silica particles modified with EDDA-methyl and activated using zirconium(IV). A 5% (v/v) suspension of the particles in water is used in accordance with the protocol shown below.

The elution buffer employed is 100 mM ammonium thiocyanate, pH 10.5, in water.

Binding and wash buffers have the following composition:
binding buffer: 1.5% (v/v) of acetic acid in water
wash buffer 1: 0.1% of acetic acid in water
wash buffer 2: 0.1% of acetic acid/30% of acetonitrile in water Equilibration of the Support Material
1. The contents of the container are mixed thoroughly with the particles in order to obtain a homogeneous suspension of the particles.
2. 50 µl of particle suspension are introduced into a microcentrifuge tube and incubated for 1 min at RT in a magnet separator (for example Dynal MPC®-S) in order to deposit the particles. The supernatant is discarded.
3. The microcentrifuge tube is removed from the magnet separator, and the particles are resuspended in 200 µl of water.
4. For deposition of the particles, the mixture is again incubated for 1 min at RT in a magnet separator (for example Dynal MPC®-S). The supernatant is discarded.
5. Steps three and four are repeated once.
6. The microcentrifuge tube is removed from the magnet separator, and the particles are resuspended in 100 µl of binding buffer.
7. For deposition of the particles, the mixture is again incubated for 1 min at RT in a magnet separator (for example Dynal MPC®-S). The supernatant is discarded.

Preparation of the Phosphopeptide Sample
1. 10-20 µl of sample solution are introduced into a microcentrifuge tube and diluted with 90 µl of binding buffer.

Enrichment of Phosphopeptides
1. The particles are resuspended in the diluted sample, and the suspension is incubated for 10 min at RT with shaking.
2. For deposition of the particles, the mixture is incubated for 1 min at RT in a magnet separator (for example Dynal MPC®-S). The supernatant is discarded.
3. The particles are resuspended in 100 µl of wash buffer 1 and subsequently, for deposition of the particles, incubated for 1 min at RT in a magnet separator (for example Dynal MPC®-S). The supernatant is discarded.
4. Step 3 is repeated
5. The particles are resuspended in 100 µl of wash buffer 2 and subsequently, for deposition of the particles, incubated for 1 min at RT in a magnet separator (for example Dynal MPC®-S). The supernatant is discarded.
6. Step 5 is repeated
7. The particles are isolated by centrifugation for 1 min at RT and 1000-2000×g. The supernatant is discarded.
8. The particles are resuspended in 25 µl of elution buffer, and the suspension is incubated for 10 min at RT with shaking.
9. The particles are isolated by centrifugation for 2 min at RT and 10,000×g.
10. The supernatant contains the enriched phosphopeptides.

Figure 6:
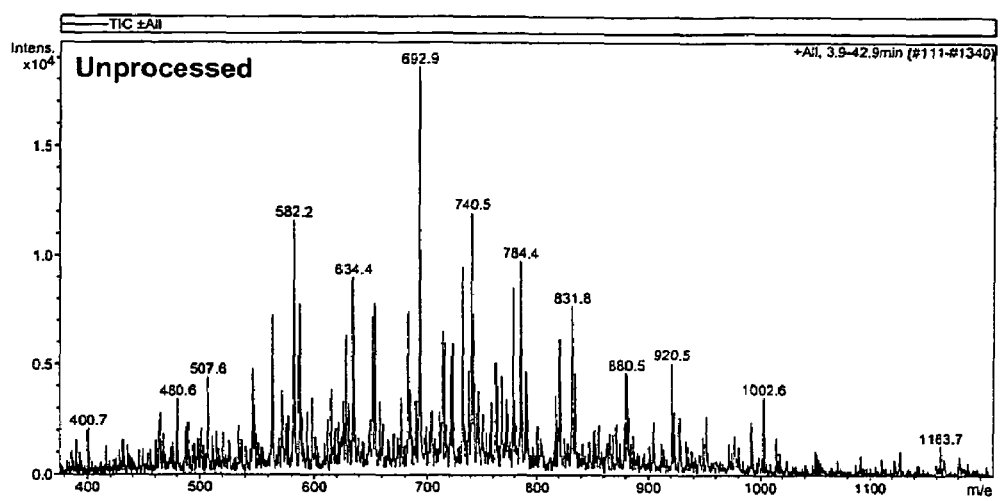
FIG. 6 shows the ESI-MS spectra of an enrichment of phosphopeptides using a preferred embodiment of the method according to the invention. Further details are given in Example 3.
Figure 6:
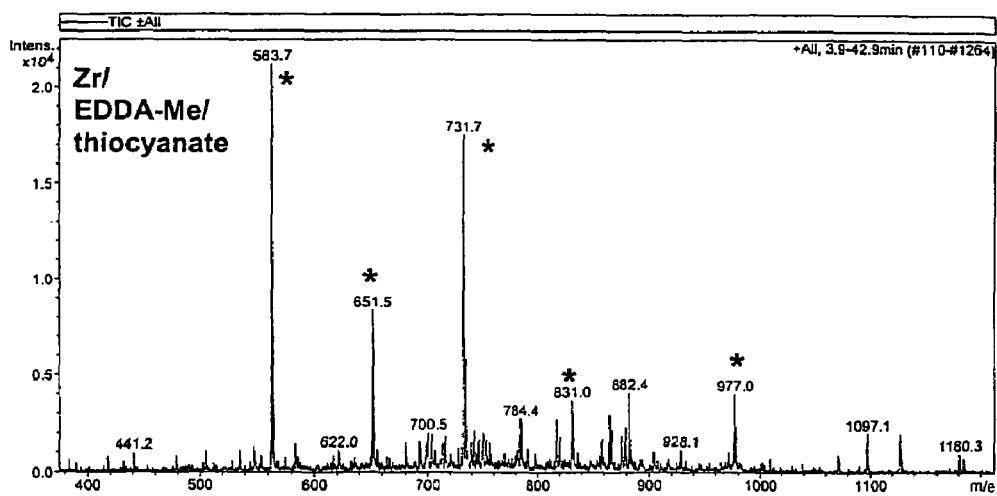

FIG. 6 shows the result of the enrichment of phosphopeptides from a complex mixture using the above-described preferred embodiment of the method according to the invention. An equimolar mixture of tryptic peptides from bovine serum albumin, histone type IIB1 and alpha-caseine and a synthetic serine-phosphorylated monophosphopeptide ($2 \times 10^{-10}$ mol per peptide) was additionally mixed with $2 \times 10^{-11}$ mol of a synthetic tyrosine-phosphorylated peptide. The sample accordingly contained about 125 expected peptides, two of which were expected serine-phosphorylated monophosphopeptides and additionally one was a tyrosine-phosphorylated monophosphopeptide, which was present in 10% of the molar amount of all other peptides. The polyphosphorylated peptide of alpha-caseine was not detected under the mass spectrometer settings used.

Representative spectra of the unprocessed sample and the eluate after affinity enrichment of phosphopeptides by the method according to the invention are shown; the phosphopeptide signals are explained in Table 8.

TABLE 8

Assignment of the phosphopeptide signals after enrichment of synthetic and natural phosphorylated peptides from a complex mixture.

| No. | m/e | Amino acid sequence | Ion | Protein/peptide |
|---|---|---|---|---|
| 1 | 563.7 | DRVpYIHPF | $[M + 2H]^{+2}$ | p-Angiotensin |
| 2 | 651.5 | YKVPQLEIVPNpSAEER | $[M + 3H]^{+3}$ | α-S1-Caseine |
| 3 | 731.7 | DLDVPIPGRFDRRVpSVAAE | $[M + 3H]^{+3}$ | Calcineurin substrate peptide |
| 4 | 831 | VPQLEIVPNpSAEER | $[M + 2H]^{+2}$ | α-S1-Caseine |
| 5 | 977 | YKVPQLEIVPNpSAEER | $[M + 2H]^{+2}$ | α-S1-Caseine |

All expected phosphopeptides are significantly enriched and are the main signals of the spectrum. The simultaneous enrichment of serine- and tyrosine-phosphorylated peptides additionally shows that the method does not distinguish between the different phosphoamino acids. The tyrosine-phosphorylated peptide is detected with m/e=563.7 for the ion $[M+2H]^{+2}$ and is significantly enriched compared with the unphosphorylated peptides in the unprocessed sample. Furthermore, the signals of the phosphopeptides represent the main signals of the spectrum, while residual impurities are virtually undetectable.

This result shows that peptides with various phosphoamino acids can be enriched simultaneously with the aid of the enrichment method according to the invention. Furthermore, it has been found that phosphopeptides which are present in substoichiometric amount in a mixture of unphosphorylated peptides can also be enriched for analysis and separated virtually quantitatively from the impurities.

4. Enrichment of Phosphopeptides by IMAC Using IDA-Modified Chromatography Materials The enrichment of phosphopeptides by IMAC using polymeric IDA-modified support materials was analysed with the aid of the test described in Example 1. In addition, IDA-modified magnetic silica particles were produced (corresponding to Example 2) and employed under identical conditions (Table 3). The metal ions employed were by way of example Ga(III), Fe(III) and Zr(IV).

The evaluation confirms that simultaneous quantitative yield and purity in the sense of the present invention cannot be achieved in accordance with the documented prior art. The best purity (85% at the same time as a yield of only 30%) was achieved using the trivalent gallium ion in combination with a polymeric support material, the highest yield (64% at the same time as a purity of only 44%) was achieved using the tetravalent zirconium ion in combination with a polymeric support material.

TABLE 3

Yield and purity in the enrichment of phosphopeptides by IMAC in accordance with the prior art using IDA-modified chromatography materials.

| Material | Modification | Metal ion | Elution | Yield [%] | Purity [%] |
|---|---|---|---|---|---|
| Polymer | IDA | Gallium (III) | 0.1 N NH$_4$OH, pH 11.2 | 30 | 85 |
| Polymer | IDA | Gallium (III) | 0.2 M Na$_3$PO$_4$, pH 8.4 | n.d. | n.d. |
| Polymer | IDA | Iron (III) | 0.1 N NH$_4$OH, pH 11.2 | 2 | 37 |
| Polymer | IDA | Iron (III) | 0.2 M Na$_3$PO$_4$, pH 8.4 | 44 | 59 |
| Polymer | IDA | Zirconium (IV) | 0.1 N NH$_4$OH, pH 11.2 | 64 | 44 |
| Polymer | IDA | Zirconium (IV) | 0.2 M Na$_3$PO$_4$, pH 8.4 | 34 | 40 |
| Silica | IDA | Gallium (III) | 0.1 N NH$_4$OH, pH 11.2 | 21 | 82 |
| Silica | IDA | Iron (III) | 0.1 N NH$_4$OH, pH 11.2 | 34 | 86 |
| Silica | IDA | Zirconium (IV) | 0.1 N NH$_4$OH, pH 11.2 | 51 | 79 |

The use of the IDA-modified magnetic silica particles in combination with methods carried out in accordance with the prior art for the binding and elution of the phosphopeptides also brings only little improvement. In particular, the yield is about 50% or less. The results of these experiments show that to date no method is known which achieves quantitative purity and yield. Using silica supports, a relative improvement in the purity achieved was observed compared with polymeric supports, but the achievable yield was unchanged and was a maximum of about 50%.

5. Analysis of the Enrichment of Phosphopeptides by the Method according to the Invention Table 4 firstly shows the enrichment of phosphopeptides by the method according to the invention (analogously to Example 3) using IDA-modified magnetic silica particles. For comparison, data are again given on the elution with hydroxide buffer in accordance with the prior art.

TABLE 4

The method according to the invention allows the quantitative elution of phosphopeptides by immobilised metal ions.

| Material | Modification | Metal ion | Elution | Yield [%] | Purity [%] |
|---|---|---|---|---|---|
| Silica | IDA | Iron(III) | 0.1 N NH$_4$OH, pH 11.2 | 34 | 86 |
| Silica | IDA | Iron(III) | 0.1 M Na$_3$PO$_4$, pH 10.5 | 99 | 76 |
| Silica | IDA | Zirconium(IV) | 0.1 N NH$_4$OH, pH 11.2 | 51 | 79 |
| Silica | IDA | Zirconium(IV) | 0.1 M Na$_3$PO$_4$, pH 10.5 | 99 | 85 |
| Silica | IDA | Zirconium(IV) | 0.1 M (NH$_4$)$_3$PO$_4$, pH 10.5 | 100 | 87 |

The table clearly shows that the method according to the invention facilitates excellent yields at the same time as very good purity.

For evaluation of the EDDA-methyl surface modification according to the invention, a novel silica surface was produced as described in Example 2 and evaluated by the test described in Example 1 with respect to the yield and purity of the isolated phosphopeptide.

The enrichment was carried out by the method as described in Example 3.

Table 5 contains illustrative data for the EDDA-Me surface modification in combination with the metals iron(III) and zirconium(IV).

TABLE 5

Yield and purity in the enrichment of phosphopeptides by IMAC using novel EDDA-methyl-modified chromatography materials.

| Material | Modification | Metal ion | Elution | Yield | Purity |
|---|---|---|---|---|---|
| Silica | EDDA-Me | Iron(III) | 0.1 M (NH$_4$)$_3$PO$_4$, pH 10.5 | 92 | 98 |
| Silica | EDDA-Me | Zirconium(IV) | 0.1 M (NH$_4$)$_3$PO$_4$, pH 10.5 | 97 | 99 |

The results show that particularly efficient enrichments are achieved with the EDDA-Me surface modification according to the invention, where R=methyl. With EDDA-Me-modified magnetic silica particles in combination with the elution method which is preferred in accordance with the invention, quantitative yield and purity were achieved simultaneously both on use of iron(III) and of zirconium(IV). Thus, an increase in the selectivity of the isolation of phosphopeptides was again achieved through the use of the novel EDDA-Me-modified magnetic silica particles compared with IDA-modified magnetic silica particles (Table 4). The purity of the isolated phosphopeptide was increased from 76% to 98% in the case of iron(III), for example, and from 87% to 99% in the case of zirconium(IV).

6. ESI-LC Mass Spectrometry Analysis of the IMAC Enrichment of Phosphopeptides with the Aid of the Support Material according to the Invention Containing the Tetradentate Chelating Agent EDDA-Me All previous analyses were carried out with a peptide mixture of low complexity in order to be able to evaluate the method according to the invention by means of simultaneous quantitative and qualitative analysis. In general, however, the samples, as indicated in the introduction, are more complex and comprise phosphopeptides in the presence of a multiplicity of unphosphorylated peptides.

In order to evaluate the selectivity of the method according to the invention for phosphopeptide enrichment by means of the novel chelating agent EDDA-methyl compared with IDA, a complex test mixture was prepared by tryptic digestion of equimolar amounts of the three proteins alpha-S1-caseine, bovine serum albumin and histone type IIB1. In the case of assumed complete tryptic cleavage, this peptide mixture comprises a monophosphopeptide of alpha-caseine in a background of 125 unphosphorylated peptides. The analysis is carried out by way of example by LC/ESI mass spectrometry. The polyphosphorylated peptide of alpha-S1-caseine cannot be analysed due to the mass spectrometer setting used. In contrast to the test method described in Example 1, however, mass spectrometry does not allow a quantitative interpretation of the result. The relative intensity of the ion signal of a certain peptide depends, apart from on its relative abundance, on a number of further parameters, such as the ionisability of the peptide.

Nevertheless, the high sensitivity of mass spectrometry makes this the detection system of choice in the analysis of phosphopeptides. Furthermore, the high sensitivity of mass spectrometry allows very good conclusions regarding the selectivity of a certain method for phosphopeptide enrichment, although the relative intensity of the phosphopeptide signal is not a quantifiable criterion for the purity of the sample for the above-mentioned reasons.

An amount of the test mixture which corresponds to 2× 10$^{-10}$ mol of each peptide was processed by the phosphopeptide enrichment method according to the invention, where either an IDA-modified silica support or an EDDA-Me-modified silica support as described in Example 2 was employed.

The enrichment method was carried out as described in Example 3, where the elution buffer comprised ammonium phosphate instead of ammonium thiocyanate.

Figure 2:
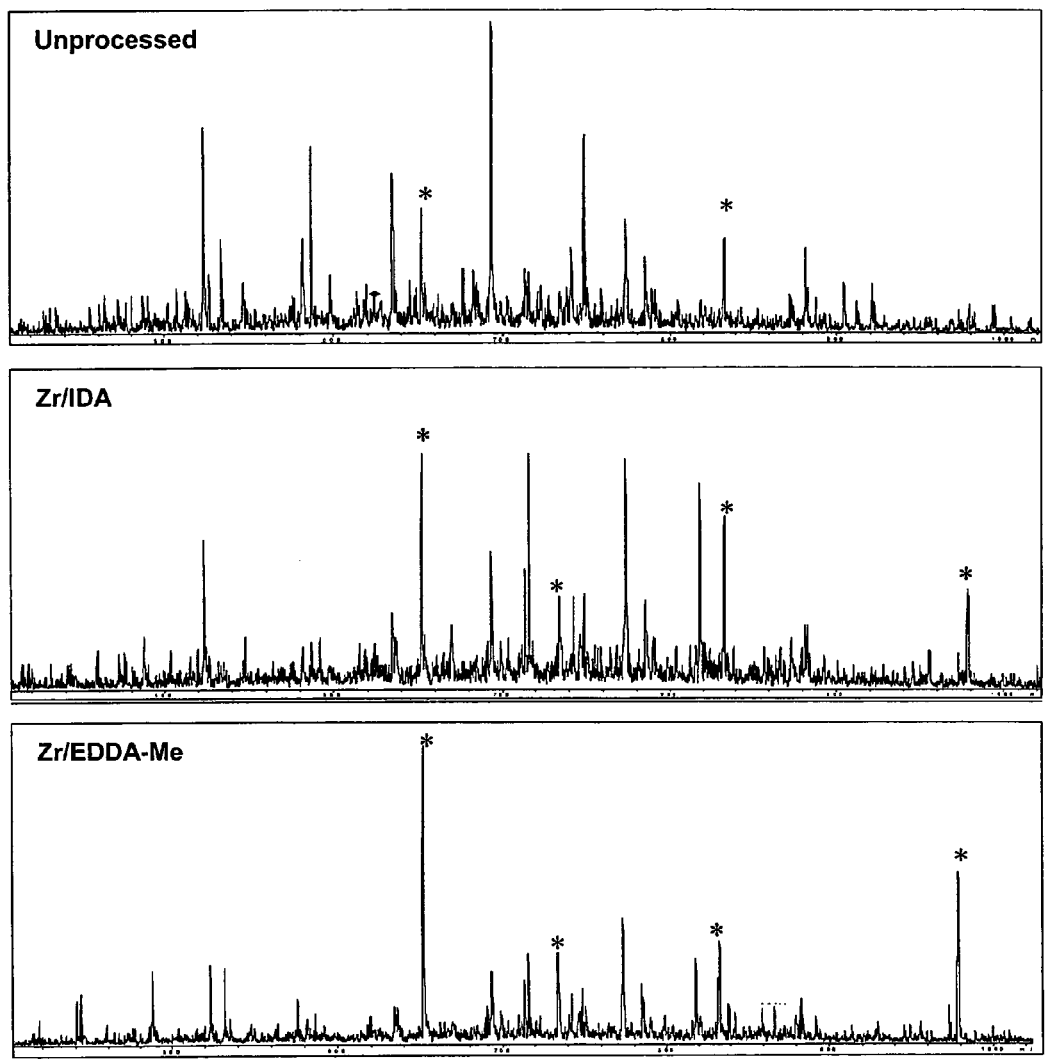
FIG. 2 shows sections of ESI-LC/MS spectra of the unprocessed sample and of bound peptides after the enrichment according to the invention. Further details are given in Example 6.

As shown by FIG. 2, a higher selectivity of the novel chelating agent EDDA-Me compared with IDA can also be documented with a complex sample in agreement with the results described above. The phosphopeptide signals detected are shown in Table 6.

TABLE 6

Assignment of the phosphopeptide signals after enrichment of phosphorylated peptides from a complex mixture.

| No. | m/e | Amino acid sequence | Ion | Protein |
|---|---|---|---|---|
| 1 | 651.4 | YKVPQLEIVPNpSAEER | [M + 3H]$^{+3}$ | α-S1-Caseine |
| 2 | 734.3 | TVDMEpSTEVFTV | [M + 2H]$^{+2}$ | α-S2-Caseine |
| 3 | 831.4 | VPQLEIVPNpSAEER | [M + 2H]$^{+2}$ | α-S1-Caseine |
| 4 | 977 | YKVPQLEIVPNpSAEER | [M + 2H]$^{+2}$ | α-S1-Caseine |

Surprisingly, three different phosphopeptides are detected, two of which (corresponding to signals ¼ and 3) are explained by incomplete tryptic cleavage of alpha-caseine and contain the same phosphorylation site of the protein. The third phosphopeptide (corresponding to signal 2) corresponds to a sequence-homologous peptide from the protein alpha-S2-caseine, which possibly was present as impurity in the alpha-S1-caseine batch used. Good results can be achieved both using the novel EDDA-methyl surface modification and also using the tridentate chelating agent IDA. However, the phosphopeptide enrichment method according to the invention using the novel EDDA-methyl surface modification allows even higher selectivity in the enrichment of phosphopeptides from complex samples than with the tridentate chelating agent IDA.

7. Direct Sample Analysis by Means of MALDI-TOF Mass Spectrometry

A promising method for phosphopeptide enrichment from complex samples should allow direct analysis of the isolated phosphopeptides, in particular by MALDI-mass spectrometry. MALDI-mass spectrometry is a very sensitive analytical technique which is generally more sensitive than ESI-LC/MS, but is influenced to a greater extent by ionic components in the sample, such as, for example, by salts.

As described above, competitive elution by alkaline earth metal and ammonium salts of orthophosphoric acid, of hydrogenphosphate or of dihydrogenphosphate at pH>10 is preferably employed in order to achieve a good yield in the elution of phosphopeptides by immobilised metal ions by the method according to the invention. In accordance with the prior art, samples with ionic impurities can be worked up by additional, poorly reproducible method steps, such as sample desalination, in general by reversed-phase purification of the peptides, before the analysis. However, a method in which these additional work-up steps can be omitted would be particularly advantageous. In order to evaluate the compatibility of the phosphoprotein enrichment method according to the invention with direct analysis by MALDI-mass spectrometry, a peptide mixture which comprises a monophosphopeptide having an expected mass $[M+H]^+$ of 2193.4 Da was employed. The peptide mixture was enriched by means of the method according to the invention as described in Example 3 using various elution buffers and the novel EDDA-Me-modified magnetic silica particles. All samples were analysed directly by MALDI-mass spectrometry without reversed-phase purification of the peptides.

Figure 3:
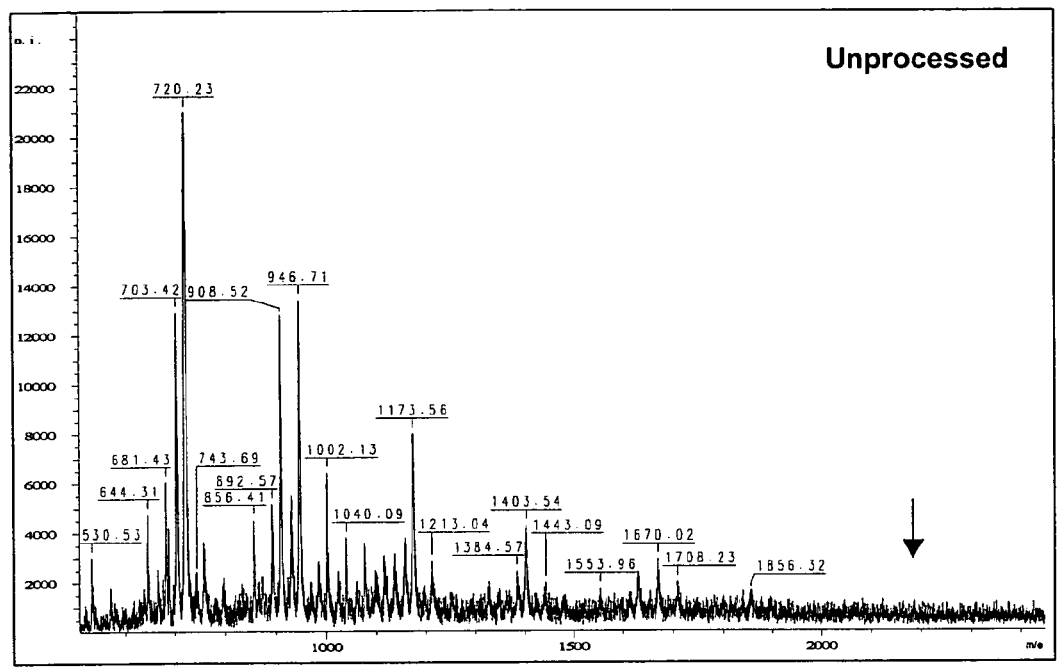
FIG. 3 shows the analysis of eluates after the enrichment according to the invention of phosphopeptides by MALDI-mass spectrometry. Further details are given in Example 7.
Figure 3:
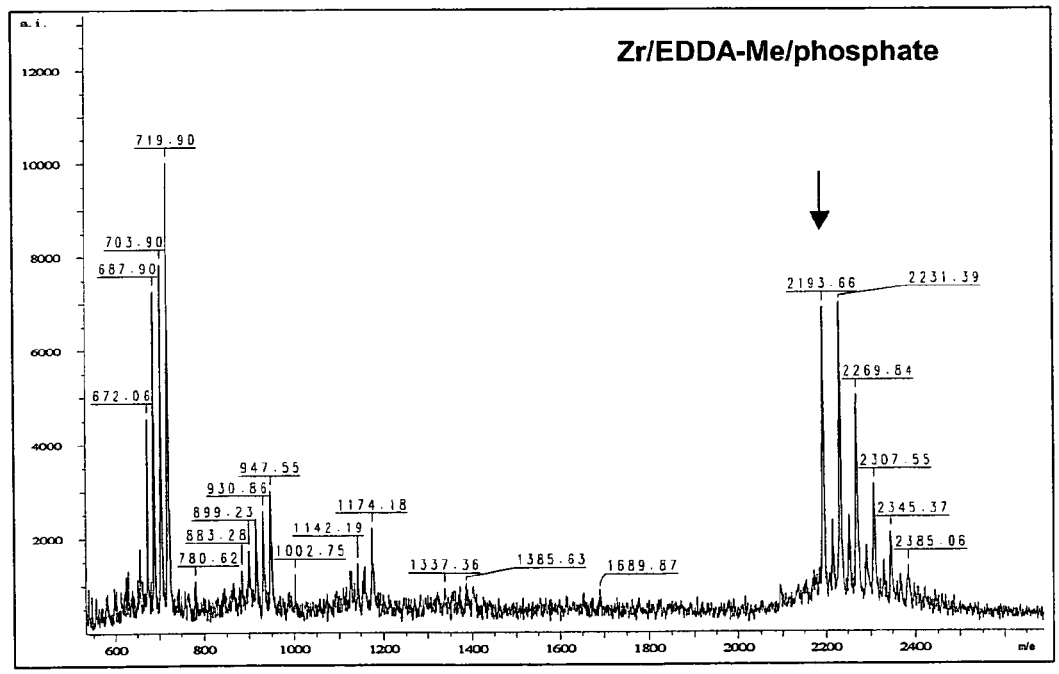

FIG. 3A shows the MALDI-MS spectrum of the unprocessed sample before enrichment. The phosphopeptide was not detected. After the enrichment according to the invention using an ammonium phosphate-containing elution buffer, by contrast, the phosphopeptide was clearly detected with m/e=2193.66, but additional masses which cannot be explained by masses of peptides present in the sample were detected (FIG. 3B). These signals are possibly artefacts caused by the phosphate ions present in the sample.

The use of the elution buffer comprising salts of thiocyanic acid which is preferred in accordance with the invention therefore represents a significant improvement.

Table 7 shows that excellent enrichment results are obtained both on use of elution buffers comprising the ammonium salt of orthophosphoric acid and also on use of an elution buffer comprising the ammonium salt of thiocyanic acid. However, this is surprisingly only possible at pH values of greater than 10 to 10.5, while a yield of only 3% was achieved, for example, at weakly acidic pH.

TABLE 7

Yield and purity in the enrichment of phosphopeptides by IMAC using novel EDDA-R-modified chromatography materials using complex ligands.

| Material | Modification | Metal ion | Elution | Yield | Purity |
|---|---|---|---|---|---|
| Silica | EDDA-Me | Zirconium(IV) | 0.1 M $(NH_4)_3PO_4$, pH 10.5 | 97 | 99 |

TABLE 7-continued

Yield and purity in the enrichment of phosphopeptides by IMAC using novel EDDA-R-modified chromatography materials using complex ligands.

| Material | Modification | Metal ion | Elution | Yield | Purity |
|---|---|---|---|---|---|
| Silica | EDDA-Me | Zirconium(IV) | 0.1 M $(NH_4)SCN$, pH 5.5 | 3 | n.d. |
| Silica | EDDA-Me | Zirconium(IV) | 0.1 M $(NH_4)SCN$, pH 10.5 | 99 | 97 |

Figure 4:
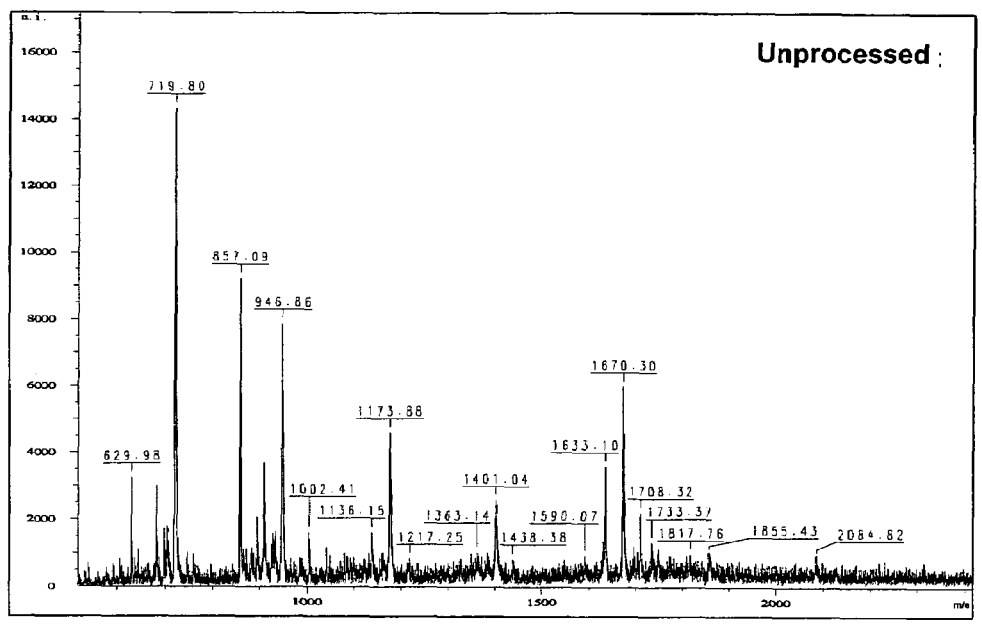
FIG. 4 shows the analysis of eluates after the enrichment according to the invention of phosphopeptides by elution with ammonium thiocyanate buffer at alkaline pH by MALDI-mass spectrometry. Further details are given in Example 7.
Figure 4:
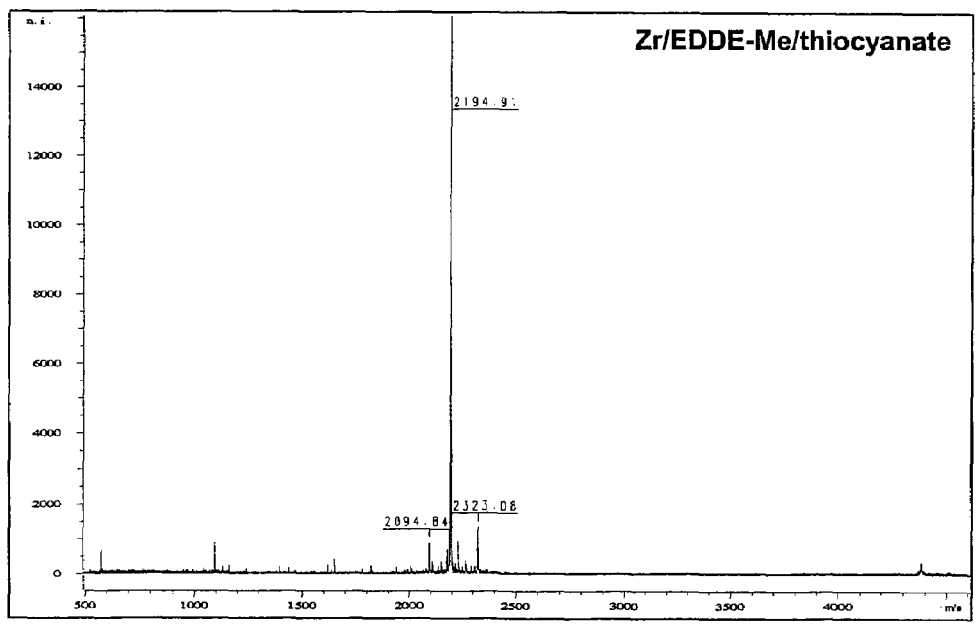

The compatibility of the phosphopeptide elution according to the invention with alkaline solutions of complex ligands was then investigated as described above by means of MALDI-mass spectrometry analysis in the case of, for example, ammonium thiocyanate, pH 10.5. All samples were again investigated directly without reversed phase purification of the peptides. As shown by FIG. 4, the phosphopeptide was not detected without prior enrichment. After the enrichment according to the invention, by contrast, the phosphopeptide was clearly detected as the only signal present with m/e=2194.91. In contrast to the use of phosphate salts for the elution (cf. FIG. 3), no unexplainable interfering signals and artefact peaks were detected after elution of the phosphopeptide by means of the thiocyanate salt. The method according to the invention for the enrichment of phosphopeptides using novel EDDA-Me-modified magnetic silica particles and complex ligands, such as the thiocyanate anion, for the elution accordingly allows for the first time simultaneous quantitative purity and yield with direct compatibility with MALDI-mass spectrometry.

8. Comparison of the Method According to the Invention with the Prior Art

Figure 5:
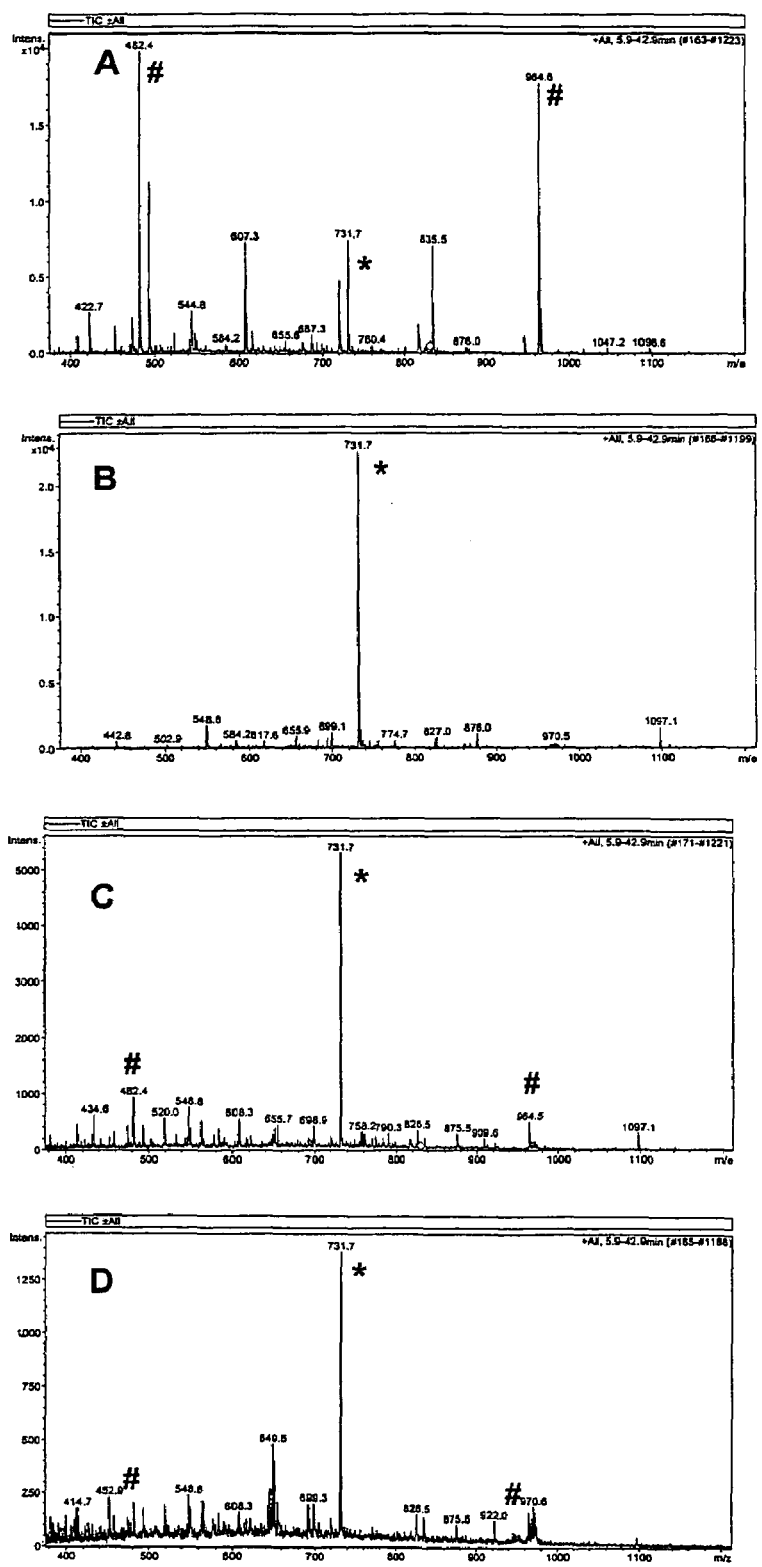
FIG. 5 shows a comparison of the enrichment according to the invention of phosphopeptides with the prior art. Further details are given in Example 8.

For comparison of the phosphoprotein enrichment method according to the invention with two commercially available methods optimised in accordance with the prior art, a mixture of three peptides (described in Example 1) was employed. The sample was processed by the method according to the invention (corresponding to Example 3) or by the procedures in accordance with the prior art, and the corresponding eluates were analysed by LC-ESI-mass spectrometry. FIG. 5 shows representative spectra of the unprocessed sample (A) and of the eluate fractions of the method according to the invention (B) as well as the methods in accordance with the prior art (C, D). The method corresponding to FIG. 5C uses a tetradentate, NTA-analogous chelating agent and iron(III) (PHOS-select iron affinity gel from Sigma), the method corresponding to FIG. 5D uses gallium(III) in combination with the tridentate chelating agent IDA (phosphopeptide isolation kit from Pierce). Both methods use polymeric supports and suggest the use of ammonium hydroxide for the elution of bound peptides.

The position of the signal of the phosphopeptide (DLDVPIPGRFDRRVpSVAAE, m/e=731.3 $[M+3H]^{+3}$) in the spectra in FIG. 5 is indicated by an asterisk, the position of the signals of two differently charged ions of the acidic peptide is indicated by a hash.

The phosphopeptide is only isolated in quantitative purity by means of the method according to the invention and can be detected with a signal intensity of $2.3 \times 10^4$ AU. The acidic peptide cannot be detected in the eluate of the method according to the invention. Both commercially available methods in accordance with the prior art, by contrast, exhibit a significantly lower relative intensity of the phosphopeptide signal of 5000 and 1500 AU respectively. In addition, the background noise due to signals of other peptides is significantly more pronounced in both samples, and the acidic peptide is clearly detected in both samples.

This shows that, in contrast to the methods carried out in accordance with the prior art, it is possible for the first time using the method according to the invention also to separate acidic peptides quantitatively and in addition to detect the phosphopeptide with very high signal intensity.

The invention claimed is:

1. Method for the enrichment of phosphopeptides, comprising of the following method steps:
   a) provision of a support material having chelate ligands based on silica
   b) activation of the support material from step a) using transition-metal ions, oxides or oxide hydrates of transition-metal ions or trivalent ions of metals from the third main group
   c) bringing a phosphopeptide-containing sample into contact with the activated support material in the presence of a binding buffer
   d) removal of the supernatant consisting of the binding buffer and the unbound part of the sample
   e) optionally washing of the support material
   f) elution of the phosphopeptides with an elution buffer which has a pH>10 and comprises alkali metal, alkaline earth metal or ammonium salts of thiocyanate, of acids of the complex ligands nitrito, isocyano, nitrile, isocyanato, isothiocyanato, azido, ethylenediamine, isonitrile, fulminato and cyano and/or of the oxygen acids of phosphorus, sulfur, vanadium, ruthenium, niobium, tantalum, tungsten or of molybdenum, and/or chelating agents.

2. Method according to claim 1, wherein the activation in step b) is carried out using iron(III) ions or zirconium(IV) ions.

3. Method according to claim 1 wherein the elution in step f) is carried out with an elution buffer which comprises of an alkali metal, alkaline earth metal or ammonium salts of oxygen acids of phosphorus or of thiocyanate in a concentration of between 0.005 and 2 mol/l.

4. Method according to claim 1, wherein the phosphopeptides eluted in step f) are investigated directly by mass spectrometry, thin-layer chromatography or by sequence analysis.

5. Method according to claim 1, wherein a support material having chelate ligands of the formula Ia and/or Ib is provided in step a)

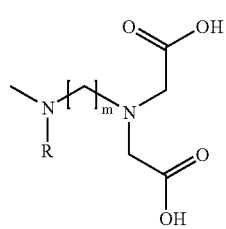

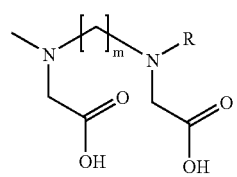

where
R=C1 to C6 alkyl or C5 to C18 aryl, optionally mono- or polysubstituted, by hydroxyl, C1-C4-alkoxy, amino, alkylamino, CN or halogen radicals, m=2 to 8, where one or more non-adjacent C atoms may be replaced by O, NH, S or —C≡C—.

6. Method according to claim 1, wherein a support material having a chelate ligand which consists of magnetite particles whose surface is at least partly covered by silica is provided in step a).

7. Kit for the enrichment of phosphopeptides, at least containing a support material having a chelate ligand based on silica and an elution buffer which has a pH>10 and comprises of an alkali metal, alkaline earth metal or ammonium salts of thiocyanate, of acids of the complex ligands nitrito, isocyano, nitrile, isocyanato, isothiocyanato, azido, ethylenediamine, isonitrile, fulminato or cyano and/or of the oxygen acids of phosphorus, sulfur, vanadium, ruthenium, niobium, tantalum, tungsten and/or molybdenum, and/or chelating agents.

8. Kit according to claim 7, wherein the support material having a chelate ligand has been activated using iron(III) or zirconium(IV) ions.

9. Kit according to claim 7, wherein the kit contains, as support material, magnetite particles which are at least partly coated with silica.

10. Kit according to claim 7, wherein the kit contains a support material having chelate ligands conforming to the formula Ia and/or Ib, where R=methyl and m=2.

11. Kit according to claim 7, wherein the kit contains, as elution buffer, a buffer which comprises alkali metal, alkaline earth metal or ammonium salts of oxygen acids of phosphorus or of thiocyanate in a concentration of between 0.005 and 2 mol/l.

* * * * *